US008261750B1

(12) United States Patent
Barry

(10) Patent No.: US 8,261,750 B1
(45) Date of Patent: Sep. 11, 2012

(54) METHOD FOR TREATING PATELLA SUBLUXATION

(76) Inventor: Patrick J. Barry, Miami Lakes, FL (US)

( * ) Notice: Subject to any disclaimer, the term of this patent is extended or adjusted under 35 U.S.C. 154(b) by 361 days.

(21) Appl. No.: 12/587,513

(22) Filed: Oct. 8, 2009

Related U.S. Application Data

(63) Continuation-in-part of application No. 11/606,314, filed on Nov. 28, 2006, now abandoned.

(51) Int. Cl.
*A61B 19/00* (2006.01)
(52) U.S. Cl. ........................................... 128/898
(58) Field of Classification Search ............... 128/898
See application file for complete search history.

(56) References Cited

U.S. PATENT DOCUMENTS

| | | | |
|---|---|---|---|
| 3,680,386 | A | 8/1972 | Cannon |
| 4,423,720 | A | 1/1984 | Meier et al. |
| 4,607,628 | A | 8/1986 | Dashefsky |
| 4,777,946 | A | 10/1988 | Watanabe et al. |
| 5,156,163 | A | 10/1992 | Watkins et al. |
| 5,554,105 | A | 9/1996 | Taylor |
| 5,556,374 | A | 9/1996 | Grace et al. |
| 5,947,913 | A | 9/1999 | Palumbo |
| 6,013,039 | A | 1/2000 | Watkins et al. |
| 6,287,269 | B1 | 9/2001 | Osti et al. |
| 6,589,248 | B1 | 7/2003 | Hughes |
| 6,702,821 | B2 | 3/2004 | Bonutti |
| 7,004,919 | B2 | 2/2006 | Gaylord et al. |
| 7,048,741 | B2 | 5/2006 | Swanson |
| 7,083,586 | B2 | 8/2006 | Simmons et al. |

OTHER PUBLICATIONS

Degowin, Robert, DeGowin's Dianostic Examination, Mcgraw-Hill Professional, 2004, p. 761.
Stefanick, Gary Low-tech Rehabilitation of Bilateral patellofemoral Knee Pain in a Runner: A Case Study, JCCA 2004, pp. 259-265.
Scuderi, Giles, The Patella, Springer 1995, pp. 41 and 79.
Ashhurst, John, The Principles and Practice of Surgery, LEA 1882, p. 300.
Runow., "The Dislocating Patella: Etiology and Prognosis in Relation to Generalized Joint Laxity and Anatomy of the Patellar Articulation" . . . No. 201 vol. 54 (1983); 1-53.
McConnell, "Management of patellofemoral problems". Manual Therapy 1 (1996): 60-66.
Van Kampen, et al, "The Three-Dimensional Tracking Pattern of the Patella in the Human Knee Joint and the Effects of Surgical Interventions". Surgery and . . . (1988): 434-445.
Dimon, "Apprehension Test for Subluxation of the Patella", Clinical Orthopaedics & Related Research 103 (1974): 39.

*Primary Examiner* — William H. Matthews
(74) *Attorney, Agent, or Firm* — Malloy & Malloy, P.L.

(57) ABSTRACT

A method for treating patella subluxation includes positioning the patient for examination of an affected knee joint. It is then determined if there is subluxation of the patella, which may occur by palpation. If subluxation is found, an affected fibrous tissue adjacent to the patella is located. This may occur through implementing imaging technology, such as live imaging where a temporally changing image of the internal components of the knee may be viewed, static imaging where a temporally fixed image of the internal components of the knee is captured, or through palpation by a practiced medical professional. An effective amount of a neurotoxin is then introduced into the affected fibrous tissue, such as through injection. The method also may include an additional step of manipulating the patella into the patellofemoral groove, which may occur manually. Thereafter, various diagnostics and exercises are implemented to monitor and rehabilitate the affected area.

26 Claims, 7 Drawing Sheets

```
          - 30 -
  Position patient for examination
```

```
          - 32 -
  Determine if there is subluxation
```

```
          - 120 -
  Locate a fibrous tissue adjacent to
              patella
```

```
          - 130 -
  Introduce an effective amount of
    neurotoxin into fibrous tissue
```

FIGURE 5

- 30 -
Position patient for examination

- 32 -
Determine if there is subluxation

- 120 -
Locate a fibrous tissue adjacent to patella

- 130 -
Introduce an effective amount of neurotoxin into fibrous tissue

- 300 -
Manipulate patella into patellofemoral groove

FIGURE 6

METHOD FOR TREATING PATELLA SUBLUXATION

CLAIM OF PRIORITY

The present application is a continuation-in-part application of previously filed, now abandoned application having Ser. No. 11/606,314, filed on Nov. 28, 2006 incorporated herein by reference in its entirety.

BACKGROUND OF THE INVENTION

1. Field of the Invention

This invention relates generally to a treatment for patella subluxation and/or tilt, and more particularly, to a method for treating this patella displacement through the introduction of a neurotoxin into the fibrous tissue of a knee joint, with an optional additional step of manual manipulation of the patella, and subsequent realignment of the patella for rapid knee pain relief without surgery.

2. Description of the Related Art

Patella instability, namely subluxation or tilting of the patella relative to the femur, is a common progressive displacement condition of the patella, occurring in all age groups. It is at times referred to as "anterior knee pain" of unknown origin, and at times as "lateral tracking syndrome". Normal alignment of the patella 2 relative to the femur 1 and tibia 3 is shown in FIGS. 1-3. With reference to FIG. 4, patella tilt is a progressive condition where the patella 2 gradually becomes laterally displaced and/or tilted relative to and against the femur 1, placing abnormal pressure on the ridge of the lateral femoral condyle 5. There are varying degrees of lateral patella tilting or subluxation. Regardless of severity, abnormal patella positioning and tilting produces an abnormal lateral and, or tilted tracking of the patella 2 against the femur 1 wherein the patella 2 glides over the lateral femoral condyle 5 rather than down in the patellofemoral groove 4. When the patella 2 becomes displaced over the lateral femoral condyle 5, at times called by the name "lateral patella tracking syndrome" or "patella compression syndrome", this causes the patella 2 to exert a progressively compressive force on the lateral femoral condyle or sulcus 5. This patella condition causes a characteristic breakdown of the articular cartilage of the patella 2 resulting in aching, grinding or pain that is typically vague in location and can extend proximally into the thigh muscles and distally into the calf muscles.

With reference to FIGS. 2-4, the knee has four muscles, the rectus femoris (not shown), the vastus lateralis 6, vastus intermedius 7 and vastus medialis 8. When walking, running or climbing, the vastus lateralis 6 pulls the patella 2 laterally, resulting in chronic thickening and contracture of the vastus lateral retinaculum 9, which is the fibrous tissue that extends from the vastus lateralis 6 into the knee joint area. Fibrous tissue in general is a connective tissue, and may comprise ligaments or tendons. In the knee joint, fibrous tissue plays a role in maintaining the patella 2 in proper alignment. Abnormalities in the fibrous tissue of the knee, such as the lateral retinaculum 9, may cause or aggravate patellar subluxation. For example, the lateral pulling of the patella 2 caused by thickening or contracture of the lateral retinaculum 9 prevents the patella 2 from properly gliding in the patellofemoral groove 4 and displaces the patella 2 over the lateral femoral condyle or sulcus 5, producing compressive forces that start the process of breaking down the articular cartilage.

Patella lateral positioning, or subluxation, may also occur as a result of damage to fibrous tissue of the knee, such as when the medial retinaculum snaps or is torn. In this situation, the corresponding lateral retinaculum 9 may overcompensate and exert a force on the patella 2 which is stronger than normal, effectively pulling the patella 2 laterally out of natural alignment and thereby producing subluxation. In another example, the fibrous tissue on the lateral side of the knee may spasm uncontrollably, or contract and be unable to relax for a period of time. This spasming or prolonged contraction may effectively pull the patella 2 from the patellofemoral groove 4, thus inducing subluxation. Moreover, the misalignment of the patella 2 cannot abate until the affected fibrous tissue, such as the lateral retinaculum 9, has been restored to its natural relaxed state.

Patellar subluxation has been traditionally treated with orally administered medication, surgery and, or knee braces. Initially, activity is limited while having the patient take medication, such as aspirin or other anti-inflammatory medicine. This approach rarely works. If the patient does not improve with these conservative measures, then surgery is typically required. The most common surgical technique is a lateral retinacular release, whereby the lateral retinaculum 9 is divided surgically by making an incision along the dotted line shown in FIG. 2.

Surgery is not always successful. It is expensive and requires a long recovery time. Knee braces are also undesirable, as they are uncomfortable and typically fail to resolve the problem. If a nonsurgical solution existed for treating a patella positioning abnormality to provide rapid knee pain relief through patellar realignment, it would avoid these shortcomings and be well received.

Unfortunately, there are no previously known practical non-surgical options for treating patella subluxation or providing rapid relief. For instance, U.S. Pat. No. 4,423,720, issued to Meier et al, discloses a patellar stabilizing orthosis brace used in conjunction with rehabilitation programs involving all nonsurgical patella dislocations or mal-alignments including chondromalacia patellae, dislocation of the patella or subluxation of the patella. U.S. Pat. No. 4,607,628, issued to Dashefsky, discloses a knee brace and includes a patella support pad positioned to engage a lateral edge of the patella. U.S. Pat. No. 5,554,105, issued to Taylor, discloses a patella stabilizer having a sleeve worn around the knee. U.S. Pat. No. 4,777,946, issued to Watanabe et al., discloses a gadget for the remedy and prevention of knee joint trouble accompanied by the movement of the patella, comprising a patella fixing member and a connecting belt wound round the knee to fix the patella fixing member thereon. U.S. Pat. No. 6,287,269, issued to Osti et al., discloses an orthesis device for the conservative treatment of patellofemoral instability of the knee. U.S. Pat. No. 6,589,248, issued to Hughes, discloses a patellar alignment device for determining the position of a patella prosthesis comprising a baseplate and a mobile component which is magnetically attached to the baseplate. U.S. Pat. No. 7,004,741, issued to Gaylord et al., discloses an apparatus for stabilizing movement of the patella in the patellofemoral joint comprising a base having an opening, a buttress secured to the base sheet member, a tensioning member secured to the base sheet member, a pair of tensioning arms secured to the buttress, a pair of tensioning arms secured to the tensioning member, a pair of compression members formed from the base, and a stabilizing member secured to an edge of the base. U.S. Pat. No. 7,048,741, issued to Swanson, discloses a method for performing an operative, minimally invasive knee arthroplasty comprising the steps of creating an incision along the medial or lateral aspect of a patient's knee, exposing the knee joint, resecting the distal end of the femur, the proximal end of the tibia and the posterior patella through the medial or lateral incision, and connecting a femoral, tibial and patellar knee replacement component through the incision.

Pursuant to the foregoing, a practical non-surgical or braceless method for reliably and effectively treating patella subluxation does not exist. Accordingly, there exists a need for such a procedure. The instant invention addresses this unfulfilled need in the prior art by providing a nonsurgical procedure for treating and alleviating patella subluxation and, or tilt as contemplated by the instant invention disclosed herein.

SUMMARY OF THE INVENTION

The instant invention comprises a method for treating patellar positioning problems without surgery, orally administered medication or mechanical devices, such as braces. The instant invention provides rapid knee pain relief through the introduction of a neurotoxin to an affected patellar fibrous tissue, such as the lateral retinaculum 9. The method of the instant invention starts with properly positioning the patient, preferably in the supine position, and exerting pressure on the patient's knee(s) with the physician's fingers and/or thumbs to determine if the patient is experiencing pain on or below the femoral condyle ridge 5 or of the distal/lateral femoral sulcus of the femur. If the patient experiences pain on or below the femoral condyle ridge 5 from the application of properly placed pressure, it indicates significant dislocation or misalignment of the patient's patella 2, thereby indicating the patient is experiencing patellar subluxation. If pain is present, the method of the instant invention continues with the following protocol to improve the position of the patella in the patellofemoral groove 4.

The method includes locating at least one fibrous tissue oriented adjacent to the patella. In at least one embodiment, this fibrous tissue may be a ligament. In one embodiment, this fibrous tissue may be the lateral retinaculum 9 which lies to the lateral side of the patellofemoral groove 4. This laterally positioned fibrous tissue may be spasming or in a state of chronic contraction, thereby causing the subluxation. In one embodiment of the present invention, locating the fibrous tissue may be accomplished by palpation of the knee joint area by a practiced physician and further identification based on the tactile contour and otherwise presentation of the fibrous tissue through the skin, as an experienced physician can readily determine. In another embodiment, locating the fibrous tissue may occur through imaging technology. This may be live imaging, wherein a clinician may view a temporally changing image of the internal components of the knee joint, such as through ultrasound technology. The imaging may also occur by static imaging, wherein a temporally fixed image of the internal components of the knee joint is produced, such as an X-ray or magnetic resonance imaging (MRI) report.

Once the fibrous tissue is located, the method includes introducing an effective, non-lethal amount of a neurotoxin into the fibrous tissue. Neurotoxins are chemicals which are known to act on nerve cells, specifically by interacting with membrane proteins. Botulinum toxin, such as the commonly known BOTOX®, is one example of such a neurotoxin. Botulinum toxin inhibits neuromuscular transmission of acetylcholine and corresponding activation of voltage-gated ion channels required for muscle contraction. Botulinum toxin therefore promotes muscle relaxation by interfering with muscle contraction.

Botulinum toxin has proven to be a popular cosmetic tool in reducing the appearance of wrinkles due to its ability to prevent or reduce muscle contraction. It is also used for the treatment of cervical dystonia (or spasming of neck muscles), severe primary axillary hyperhidrosis (or excessive sweating), strabismus (or crossed eyes), and blepharospasm (or eyelid spasms) associated with dystonia. It has not, however, heretofore been used for application in fibrous or connective tissue, such as ligaments, or to affect the positioning of bones.

Botulinum toxin is still, however, a toxin, and in large doses can be fatal. It is therefore understood that the method of the present invention contemplates using only an effective amount of neurotoxin, which is an amount sufficient to promote relaxation of the affected fibrous tissue and inhibit spasming or contraction of the same once introduced, without causing fatal harm to the patient. In a preferred embodiment, the effective amount of neurotoxin may be applied non-surgically by injection into the fibrous tissue via syringe or other subcutaneous means. It is contemplated, however, that the neurotoxin may be applied to the fibrous tissue during a surgical procedure in which the internal components of the knee are otherwise exposed, such as during knee arthroplasty.

In one embodiment, the method further includes the step of manipulating the patella to enhance the improvement of the position of the patella in the patellofemoral groove. In this step, pressure is applied to the lateral mid-border of the patella in a direction away from a femur so as to begin to reduce the tilt of the subluxed patella. At the same time, pressure is also applied to the inner medial border of the upper surface of the patella to counter the tendency of medial patella drift caused by the aforementioned lateral elevation. To further reduce the tilt of the patella, pressure is then applied to the upper medial border of the patella in a direction toward the patellofemoral groove. A rocking motion is then imparted on the patella by alternately pushing on the lateral patellar border in a direction toward the patellofemoral groove and then away from the femur until space is created on the posterior side of the patella, preferably enough space to allow application of pressure to the posterior side of the patella. The posterior side of the patella is the side that corresponds to and interacts with the patellofemoral groove, i.e. the side which is opposite from the side of the patella that faces outwardly from the body. The rocking motion is then repeated by changing the lateral pressure points to the portion of the patella most proximal, or close, to the patellofemoral groove, and then to the portion of the patella most distal, or furthest from, the patellofemoral groove until the patella is returned to a substantially normal configuration within the patellofemoral groove. Once the aforementioned steps are completed, the patient is examined to determine whether there is any improvement by having the patient walk, flex the knee, rise from a sitting position and climb steps. In one embodiment, the protocol of the instant step comprises approximately three sessions to not only improve the patellar position, but to maintain it. In one embodiment of the additional step of manipulating the patella, such manipulation may be accomplished manually by a trained individual. However, it is understood that neither the trained individual nor body parts thereof are claimed in the present invention, but are referenced herein merely to better explain the method of the present invention. It is further appreciated that the step of manipulating the patella of one embodiment of the present invention can occur through any means in which pressure or force can be applied to affect the positioning of the patella, and may not involve the use of hands, fingers, or parts of a trained individual at all.

In accordance with these and other objects, which will become apparent hereinafter, the instant invention will now be described with particular reference to the accompanying drawings.

BRIEF DESCRIPTION OF THE DRAWINGS

For a fuller understanding of the nature of the present invention, reference should be had to the following detailed description taken in connection with the accompanying drawings in which:

FIG. 5 is a flow diagram of the steps of one preferred embodiment of the method of the instant invention.

FIG. 6 is a flow diagram of another embodiment of the method of the instant invention.

Like reference numerals refer to like parts throughout the several views of the drawings.

DETAILED DESCRIPTION OF THE PREFERRED EMBODIMENT

Figure 1:
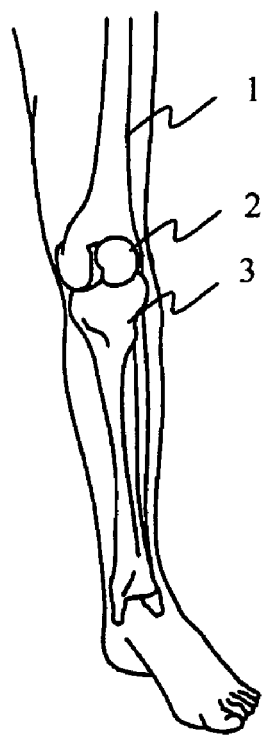
FIG. 1 is an elevational diagram of a patella and femur showing normal congruity of the femur, patella and tibia.
Figure 2:
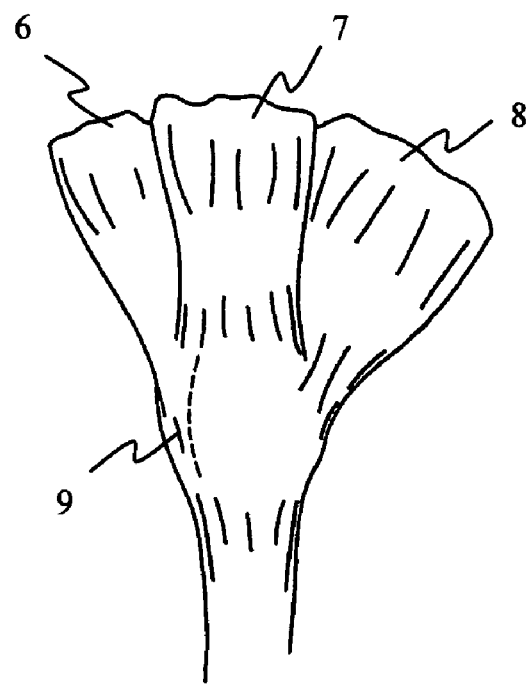
FIG. 2 is an elevational diagram of a knee showing the vastus lateralis, vastus intermedius and vastus medialis, which are three of the four muscles of the quadriceps group, with a dotted line to show the location of the lateral retinaculum and the site for operative incision.
Figure 3:
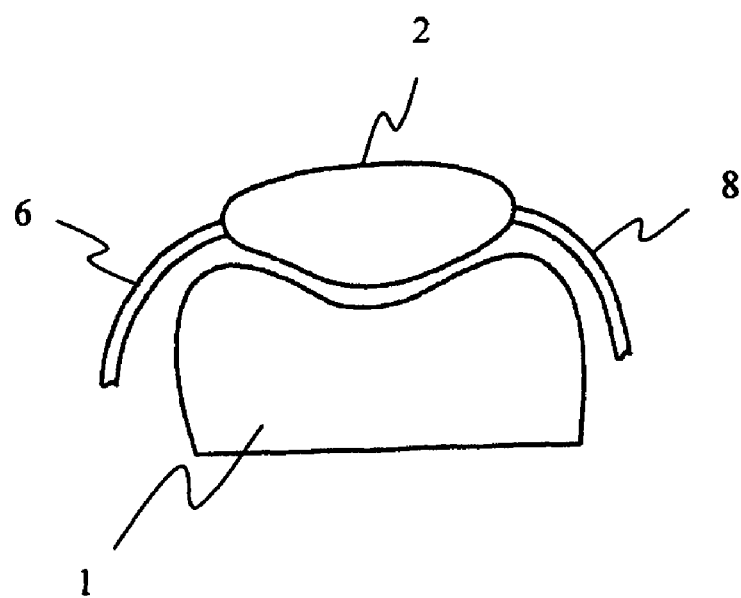
FIG. 3 is a planar view of the patella and femur showing normal congruity between the patella and femoral joint.
Figure 4:
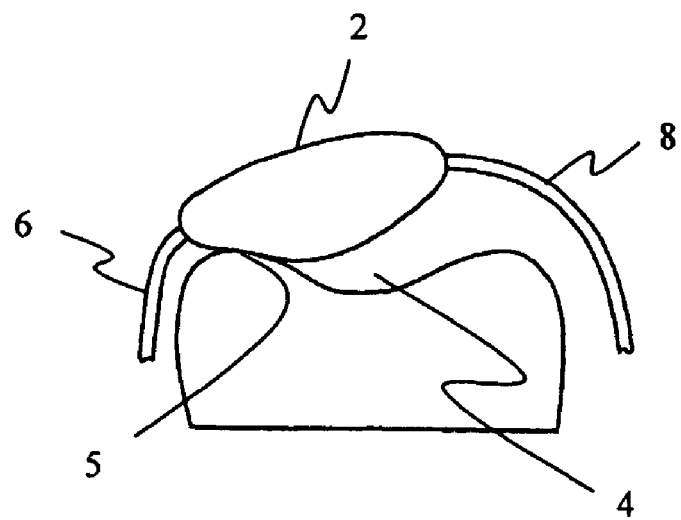
FIG. 4 is a planar view of the patella in relation to the femur showing patellar abnormal positioning in the form of lateral tilt of the patella.

The instant invention comprises a method for treating patella subluxation without surgery, oral medication or mechanical devices, such as braces. The instant invention comprises a non-surgical process for treating subluxation and, or tilting of the patella 2 relative to the femur 1, referenced herein as patella subluxation. Referring to FIGS. 5 through 9c, one preferred embodiment of the patella subluxation treatment process 100 of the instant invention comprises the process of injecting an effective amount of neurotoxin into a fibrous tissue adjacent to the patella 2 to relax the fibrous tissue and restore a natural configuration of the patella 2 within the patellofemoral groove 4. Another embodiment of the method of the present invention 200 comprises injecting an effective amount of neurotoxin into a fibrous tissue adjacent to the patella 2, and manipulating 300 the patella 2 so as to gradually reposition the patella 2 in the patellofemoral groove 4 of the femur 1. This manipulating 300 of the patella 2 may occur manually, or by any other means of applying pressure or force to the patella 2. One embodiment of the instant invention 200 changes the position of a symptomatic wayward patella 2 by application of a neurotoxin to relax the fibrous tissue of the knee joint, as well as changing the abnormal contact of the patella 2 with the ridge of the lateral femoral condyle or sulcus 5.

The process 300 of manually manipulating the patella 2 generally comprises the steps of positioning the patient for examination (30), isolating the area of pain or discomfort to ascertain whether there is patella subluxation (32), manipulating the patella 2 with lateral and downward force to gradually maneuver the patella 2 back into better position within the femur's patellofemoral groove 4 (34-42), checking for improvement in patella repositioning (44) and repeating each step (46) if necessary, possibly three or more times or until the patella 2 is better reoriented to correct patella displacement and, or tilting. The manual manipulation step 300 of one embodiment 200 of the instant invention may be repeated by a physician, care taker or the individual if properly trained with the protocol for the same.

Figure 7:
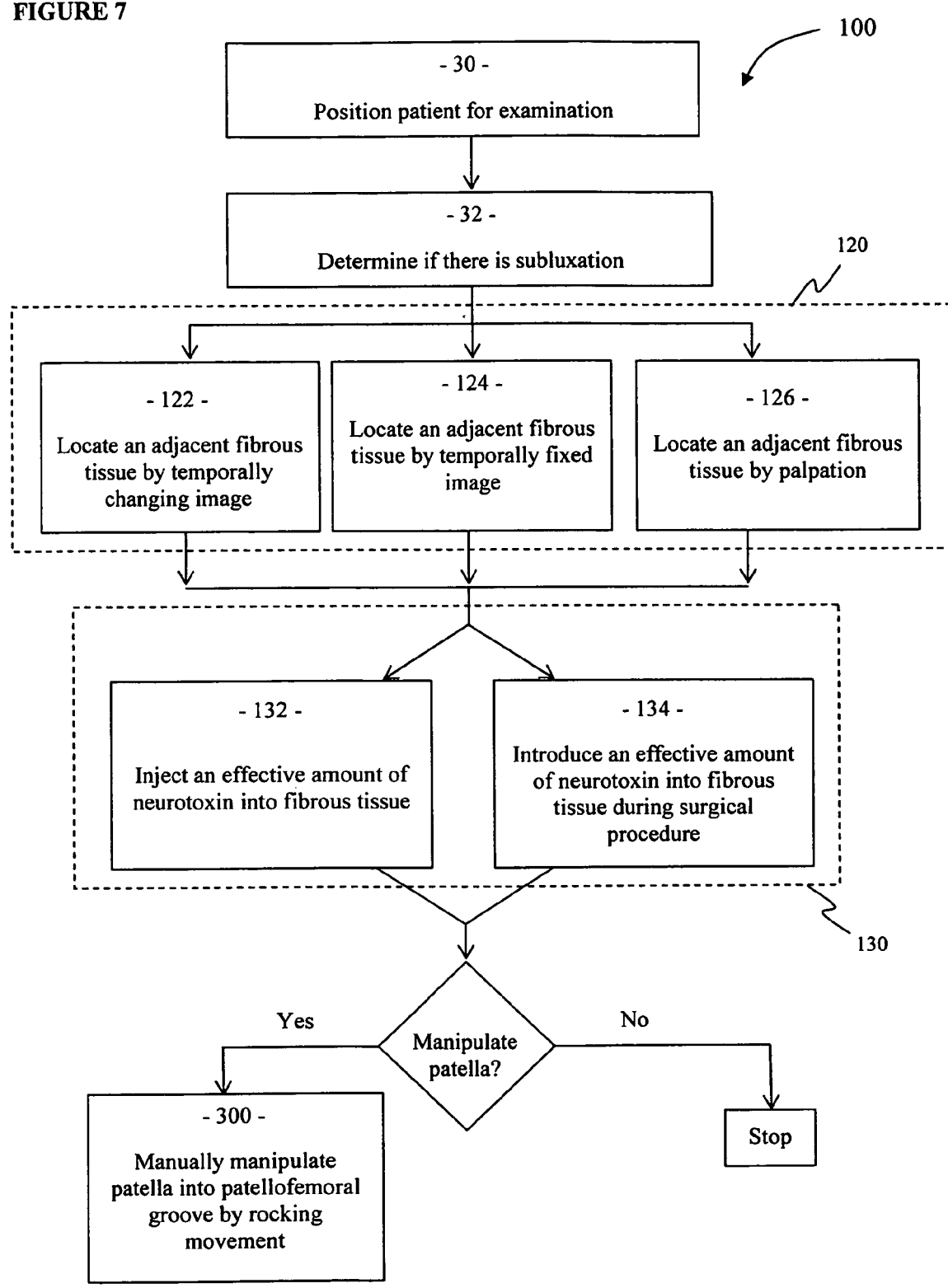
FIG. 7 is a flow diagram of the method of the present invention.

Referring now to FIGS. 5 and 7, the patella treatment method 100 of the instant invention begins with positioning a patient for examination 30. In this position, the patient may be supine or sitting, or in any other position which will allow adequate access to the knee joint for examination and treatment. Once positioned, the method 100 proceeds by determining whether the patient is experiencing patellar subluxation 32. This may be accomplished by palpating the lateral femoral sulcus ridge 5 while the patient is preferably supine, or alternatively sitting, to determine whether there is pain on the femoral ridge 5 and its distal portion on or below the ridge when touched. Pain experienced during this exam indicates that the patient has significant patellar misdirection and abnormal contact, i.e. subluxation, requiring treatment. If patella subluxation is diagnosed, the method 100 of the instant invention continues with locating an affected fibrous tissue adjacent to the patella 120. Such an affected fibrous tissue may be a ligament or tendon that is experiencing an abnormal state. Examples of an abnormal state include spasming or extended contraction of the fibrous tissue.

As is shown in FIG. 7, the step of locating an affected fibrous tissue 120 may occur through a variety of ways. For instance, locating a fibrous tissue may be achieved by utilizing imaging technology to capture an image of the internal components of the knee joint or area surrounding the patella 2, and thereby identify the location of fibrous tissues such as ligaments and tendons in relation to the patella 2. In one embodiment, this imaging may occur by live imaging, such as locating a fibrous tissue by production and utilization of a temporally changing image 122. In this embodiment, a device may be used that allows real-time viewing of the internal components of the knee and produces an image of the same that may change as internal components of the knee move, or as the device is moved from one location to another. For example, live imaging may occur by use of ultrasound technology or a sonogram, or any other medical imaging device that permits viewing of internal body components wherein the image produced may change substantially simultaneously with the changes of the body being imaged or the location of the imaging device thereon.

In another embodiment, as shown in FIG. 7, imaging may occur by static imaging, such as locating a fibrous tissue by production and utilization of a temporally fixed image 124. In this embodiment, an imaging device may be used to capture a fixed image of the internal components of a knee joint at a particular point in time. By way of example only, such static imaging may occur through the use of magnetic resonance imaging (MRI), X-ray, fluoroscopy, photoacoustic imaging, or any other technique wherein the position of internal components at a given time may be viewed and captured in image form, much like a photograph.

In yet another embodiment of the invention 100 as depicted in FIG. 7, locating a fibrous tissue adjacent to a patella may also occur by palpation 126, wherein the knee joint or area surrounding the displaced patella 2 is palpated by a practiced physician or medical professional. Such trained medical professional or physician will readily be able to identify components of the knee joint by feel through the skin during palpation, such as by recognizing the differing contours and resistance of fibrous tissues from those of muscle and bone. Based on the feel or tactile presentation of internal components of the knee during palpation and the physical relation of these components to each other, a trained physician or medical professional can readily locate an affected fibrous tissue for further application of the present invention 100.

The fibrous tissue affected in the knee may be any fibrous tissue which could affect the position of the patella 2 in relation to the patellofemoral groove 4. For instance, common fibrous tissues include ligaments and tendons. In particular, the knee contains both a medial retinaculum and a lateral retinaculum 9. In patellar subluxation, the patella 2 is misaligned laterally, which in some cases may be the result of an over-contracted lateral retinaculum 9. The invention herein provides a method 100 for relaxing such fibrous tissues. In one embodiment, the affected fibrous tissue may be a ligament. In another embodiment, the affected fibrous tissue may be the lateral retinaculum 9.

Figure 8:
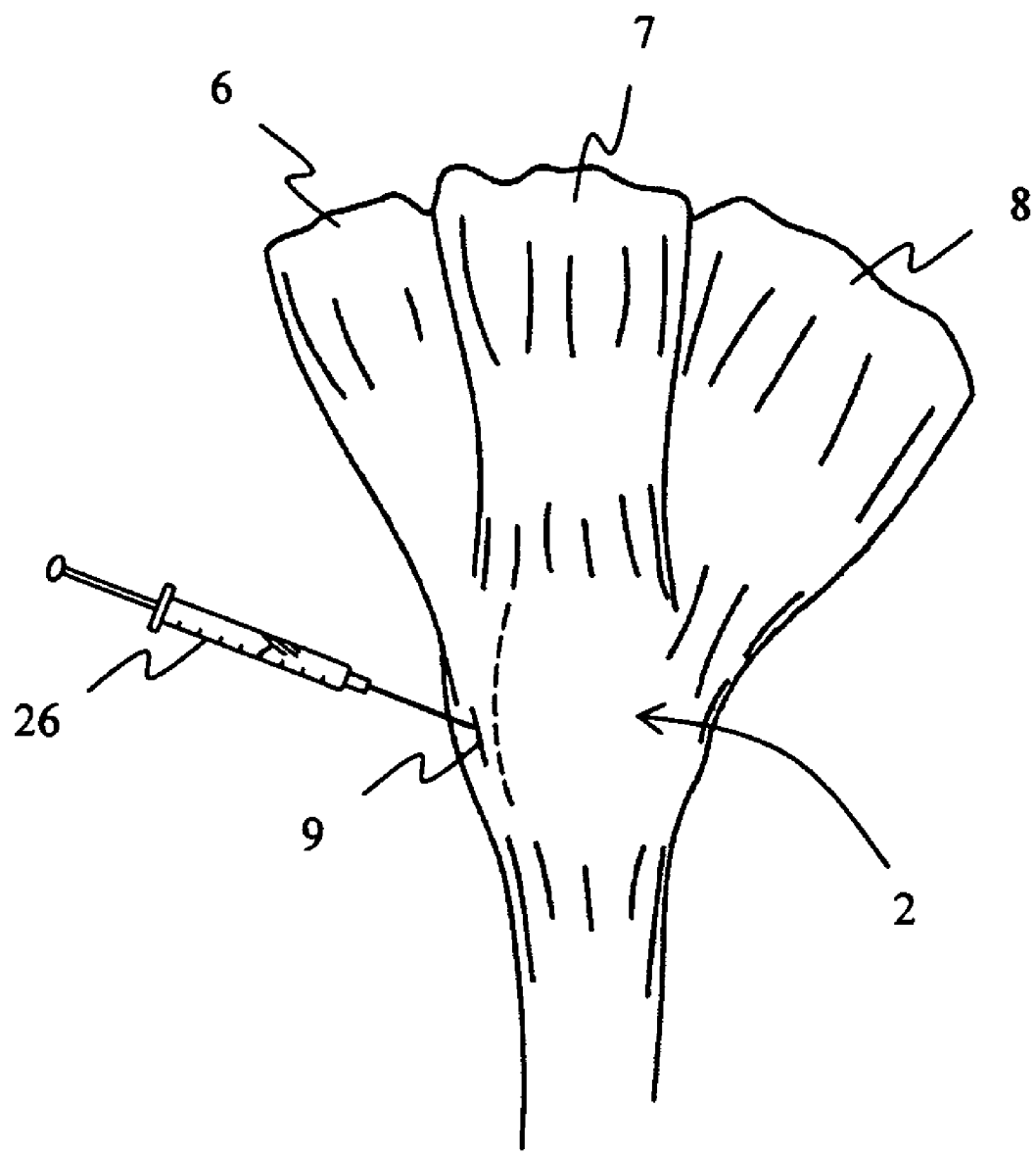
FIG. 8 is an elevational diagram of a knee showing the point of insertion of a syringe for introduction of a neurotoxin into a fibrous tissue of the knee.

Once the affected fibrous tissue is located, the method 100 further includes the step of introducing an effective non-lethal amount of neurotoxin into the fibrous tissue 130, as shown in FIGS. 5 through 8. This step may be accomplished by any means which will deliver the desired amount of neurotoxin into the fibrous tissue without requiring surgery. One embodiment, depicted in FIG. 7, contemplates introduction by injection via syringe 132, wherein the needle of the syringe 26 is inserted into the knee joint and into the fibrous tissue in order to deliver the neurotoxin to that specific tissue. FIG. 8 shows an elevational view of a knee that is receiving the introduction of neurotoxin by injection of a syringe 26 containing the neurotoxin into the fibrous tissue of the knee. In one embodiment, the neurotoxin is injected by syringe 26 into the lateral retinaculum 9 of the knee joint to affect the positioning of the patella 2. In light of the mechanism of action of neurotoxins, it is important that correct placement of the syringe 26 is achieved in order to ensure proper introduction of the neurotoxin into the targeted fibrous tissue rather than surrounding muscle, cartilage, or other components of the knee joint area. This is a delicate procedure, and care should be taken in the administration of neurotoxin. For these reasons, a trained medical professional should administer the injection 132.

And while the invention 100 is directed to treating patellar subluxation without surgery, it is nevertheless contemplated that if surgery were otherwise undertaken, such as knee arthroplasty for arthritis or patella replacement, the present invention 100 may also be used concurrent to the surgery. As depicted in FIG. 7, introduction of the neurotoxin to the affected fibrous tissue may occur by application of the neurotoxin to a fibrous tissue already exposed during surgery 134. This may include topical application of the neurotoxin to the exposed fibrous tissue, injection into the fibrous tissue, or any other appropriate means given the parameters and circumstances of the surgery.

It is appreciated that any neurotoxin may be used in the present invention, wherein a neurotoxin is an agent that acts on nerve cells to interfere with ion channels. In one embodiment, the neurotoxin is botulinum toxin. Other examples may include, but are not limited to, tetrodotoxin, batrachotoxin, maurotoxin, and taicatoxin. Furthermore, given that neurotoxins may be harmful if misused, the invention 100 contemplates using an effective amount of a neurotoxin, which is an amount at least enough to promote relaxation of the target or affected fibrous tissue and inhibit the tendency of the fibrous tissue to spasm and/or contract without causing undue harm to the tissue. This effective amount is well below any amount which may be lethal to the patient. The precise amount may be determined based on body weight of the patient, or other appropriate means or calculations.

Referring now to FIG. 6, another embodiment of the invention 200 comprises all of the steps discussed above, namely positioning of a patient for examination 30, determining if there is subluxation 32, locating a fibrous tissue adjacent to the patella 120, and introduction of an effective non-lethal amount of neurotoxin into the fibrous tissue 130, and further includes the additional step of manipulating the patella into the patellofemoral groove 300. The following protocol may be used to reposition the patella 2 in the patellofemoral groove 4, preferably with the physician's or other trained person's hands, although any means of applying force or pressure to relocate the patella 2 may be implemented to achieve manipulation 300.

Figure 9A:
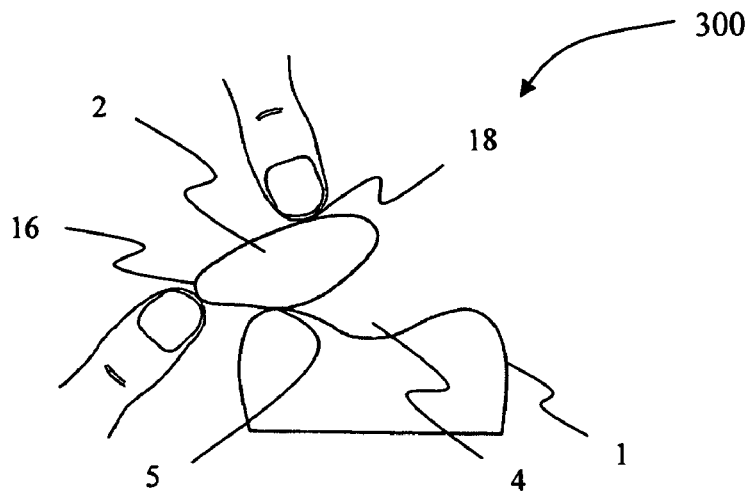
FIG. 9a is a planar view of the patella and femur showing an initial step of the manual manipulation step of the invention.
Figure 9B:
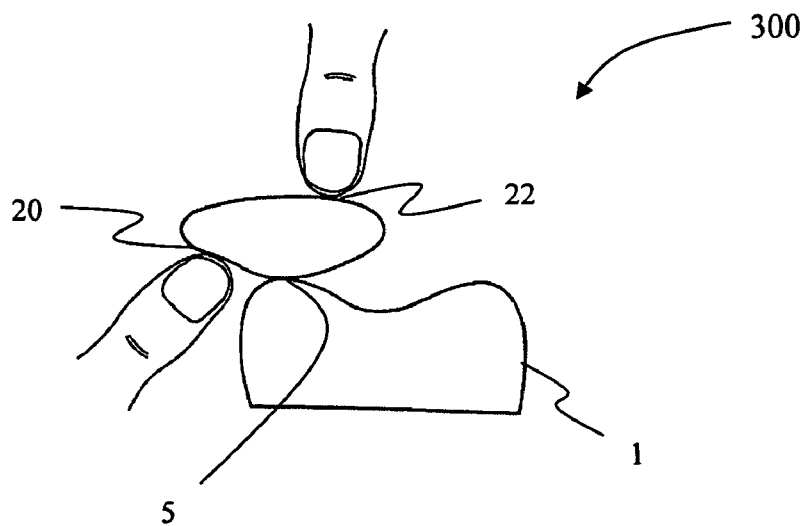
FIG. 9b is a planar view of the patella and femur showing an intermediate step of the manual manipulation step of the invention.
Figure 9C:
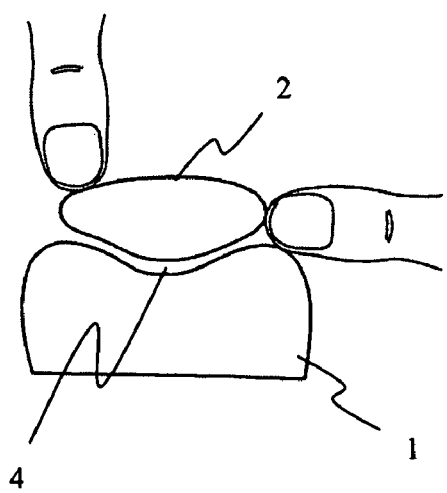
FIG. 9c is a planar view of the patella and femur showing a final component step of the manual manipulation step of the invention.

FIGS. 9a through 9c show one embodiment of the manipulation step 300 of the invention 200 in which the fingers of a trained individual are used for the application of pressure. It bears repeating, however, that the fingers and body parts of a trained professional are not claimed in the present invention, and that manual manipulation is only one of many ways in which the manipulation step 300 may be achieved. As shown in FIG. 9a, the angle of tilt of the patella 2 is reduced by applying increasingly firm pressure on the lateral mid-border 16 of the patella 2 in a direction away from a femur. Concurrently, pressure is also applied to the inner medial border 18 of the upper surface of the patella 2 in a direction toward the patellofemoral groove 4 to counter the tendency of medial patella drift caused by the aforementioned lateral elevation. Turning to FIG. 9b, to further reduce the tilt of the patella 2, pressure is applied to at least a portion of the medial border of the patella 2 in a direction toward the patellofemoral groove 4. In one embodiment, this is accomplished by pushing the upper medial border 22 of the patella 2 into the patellofemoral groove 4. A rocking motion is then imparted on the patella 2 by alternately pushing or applying pressure on a medial border, such as the upper medial border 22 of the patella in a direction toward the patellofemoral groove and pushing or applying pressure on a lateral border, such as the lateral mid-border 16 of the patella, in a direction away from a femur until sufficient space is created under the patella 2, preferably enough space to allow for the application of pressure or force to the posterior side of the patella 2. It is appreciated that the posterior side of the patella 2 is the side which corresponds and fits into the patellofemoral groove 4. In the embodiment depicted in FIG. 9b, the sufficient amount of space on the posterior side of the patella 2 may be at least enough to receive a thumb or finger. It is intended, however, that the manipulation 300 of the patella 2 may occur without the use of portions of a trained individual's body, as discussed previously. The rocking motion is then repeated by changing the lateral pressure points to a proximal portion 20 of the patella 2 and then to a distal border of the patella 22 relative to the patellofemoral groove 4 until the patella 2 is returned to a natural configuration within the patellofemoral groove 4, as shown in FIG. 9c. A natural configuration within the patellofemoral groove 4 is intended to mean the position of the patella 2 within the patellofemoral groove 4 through which the patella 2 may glide and track during movement of the knee joint without causing significant pain, i.e. a configuration which is not subluxation.

Once the aforementioned steps are completed, the patient is examined to determine whether there is any improvement by having the patient walk, flex the knee, rise from a sitting position and climb steps (Step 44). In one embodiment, the protocol of the manipulation step 300 requires approximately three sessions to reposition the patella 2 in the patellofemoral groove 4. Another embodiment of the manual manipulation step 300 may require fewer treatments when performed as the invention 200 is described herein. Still another embodiment contemplates only a single treatment of the manual manipulation step 300 of the present invention 200 to be effective.

The instant invention also has the benefit of providing information to ascertain whether patella subluxation is the condition of concern and whether there is a temporary or permanent solution to the patient's complaints of knee pain. The instant invention also addresses other conditions that can be temporarily or permanently relieved by the patella treatment process including peripheral neuropathy, patellar tendonitis, symptomatic medial plica, hypertrophy of the infrapatellar tendon fat pad, osteoarthritis, meniscal tear and chondromalacia. These conditions may really be asymptomatic, but by relieving the abnormal patella-femoral contact, the patient's knee pain from these locations is resolved.

Other conditions which are improved or resolved about the knee by employing the instant invention for patellar redirection include anterior knee pain, pain of failed surgery, occasionally early reflex sympathetic dystrophy, and recurrent dislocation of the patella.

The instant invention also includes steps for allowing the patient to continue rehabilitation. Once knee pain is partially or completely resolved by the patella treatment process, then improvement can often be maintained by teaching the patient to increase strength of the vastus medialis muscle 8. This may include vastus medialis 8 strengthening using biofeedback training. The biofeedback training is directed to strengthening the vastus medialis, or obliqous, muscle 8.

The present invention does not necessarily require the treatment to be anatomically perfect for complete relief of patellar pain. For instance, a 15% position change may provide complete or partial pain relief. The amount and length of required treatment under the instant invention may vary. For instance, simple application of the neurotoxin to the fibrous tissue may be sufficient for certain patients to have marked reductions in aches, pressure, pain, grinding, locking, swelling, and catching. In another embodiment, with the added step of manual patella manipulation, even two seconds of manipulation may be sufficient for a patient to experience relief. The process of the instant invention may in many instances eliminate the need for surgical management of the above listed problems. This may be significant, since time out of work with surgery is usually one to six weeks.

The instant invention has been shown and described herein in what is considered to be the most practical and preferred embodiment. It is recognized, however, that departures may be made therefrom within the scope of the invention and that obvious structural and/or functional modifications will occur to a person skilled in the art.

Since many modifications, variations and changes in detail can be made to the described preferred embodiment of the invention, it is intended that all matters in the foregoing description and shown in the accompanying drawings be interpreted as illustrative and not in a limiting sense. Thus, the scope of the invention should be determined by the appended claims and their legal equivalents.

Now that the invention has been described,

What is claimed is:

1. A method for treating subluxation of a patella in a patient, said method comprising:
    positioning the patient for examination,
    determining whether the patient is experiencing patella subluxation at a knee joint,
    locating at least one fibrous tissue having an orientation adjacent to the patella,
    introducing an effective amount of neurotoxin into the at least one fibrous tissue, and
    allowing the fibrous tissue to relax and restore a natural configuration of the patella within the patellofemoral groove.

2. The method as recited in claim 1 wherein determining whether the patient is experiencing patella subluxation comprises palpating the knee joint.

3. The method as recited in claim 1 wherein locating the at least one fibrous tissue includes palpating the knee joint and identifying the at least one fibrous tissue by tactile presentation.

4. The method as recited in claim 1 wherein locating the at least one fibrous tissue includes utilizing imaging technology on the knee joint.

5. The method as recited in claim 4 wherein utilizing imaging technology on the knee joint comprises creating a temporally changing image of internal components of the knee joint.

6. The method as recited in claim 4 wherein utilizing imaging technology on the knee joint comprises creating a temporally fixed image of internal components of the knee joint.

7. The method as recited in claim 1 comprising defining the at least one fibrous tissue as a ligament.

8. The method as recited in claim 1 further comprising introducing the neurotoxin into a lateral patellar retinaculum.

9. The method as recited in claim 1 further comprising defining an effective amount of neurotoxin as an amount at least enough to promote relaxation and inhibit contraction of the at least one fibrous tissue.

10. The method as recited in claim 1 wherein introducing an effective amount of neurotoxin includes injecting an effective amount of the neurotoxin into the at least one fibrous tissue.

11. The method as recited in claim 1 wherein introducing an effective amount of neurotoxin includes applying an effective amount of neurotoxin to the at least one fibrous tissue during a surgical procedure.

12. The method as recited in claim 1 wherein the neurotoxin is botulinum toxin.

13. A method for treating subluxation of a patella from a patellofemoral groove in a patient, said method comprising:
    positioning the patient for examination,
    determining whether the patient is experiencing pain on a femoral ridge,
    locating at least one fibrous tissue having an orientation adjacent to the patella,
    introducing an effective amount of neurotoxin into the at least one fibrous tissue, and
    manipulating the patella into the patellofemoral groove.

14. A method as recited in claim 13 wherein locating the at least one fibrous tissue includes palpating a region surrounding the patella and identifying the at least one fibrous tissue by tactile presentation of the at least one fibrous tissue.

15. A method as recited in claim 13 wherein locating a fibrous tissue includes imaging a region surrounding the patella.

16. A method as recited in claim 15 wherein imaging a region surrounding the patella includes creating a temporally changing image of internal components of the region surrounding the patella.

17. A method as recited in claim 15 wherein imaging a region surrounding the patella includes creating a temporally fixed image of internal components of the region surrounding the patella.

18. The method as recited in claim 13 further comprising defining the at least one fibrous tissue as a lateral patellar retinaculum.

19. A method as recited in claim 13 wherein introducing an effective amount of neurotoxin includes injecting the effective amount of neurotoxin into the at least one fibrous tissue.

20. A method as recited in claim 13 further comprising introducing an effective amount of botulinum toxin into the at least one fibrous tissue.

21. A method as recited in claim 13 further comprising manually manipulating the patella into the patellofemoral groove.

22. A method as recited in claim 13 wherein manipulating the patella further comprises applying elevating pressure to a lateral border of the patella.

23. A method as recited in claim 22 wherein manipulating the patella further comprises simultaneously applying pressure to a lateral border of the patella in a direction away from a femur and applying pressure to a medial border of the patella in a direction toward the patellofemoral groove.

24. A method as recited in claim 23 wherein manipulating the patella further comprises applying increasing pressure to at least a portion of the medial border of the patella in the direction of the patellofemoral groove.

25. A method as recited in claim 24 wherein manipulating the patella further comprises rocking the patella by alternately applying pressure to a lateral border of the patella in a direction away from a femur and pressure to a medial border of the patella in a direction toward the patellofemoral groove until a sufficient space is created to allow for the exertion of pressure to a posterior side of the patella.

26. A method as recited in claim 25 wherein manipulating the patella further comprises continuing rocking the patella by alternately applying pressure in a direction away from the femur to a portion of the patella disposed proximal to the patellofemoral groove and applying pressure in a direction toward the patellofemoral groove to a portion of the patella disposed distal to the patellofemoral groove until the patella achieves a normal and improved configuration within the patellofemoral groove.

\* \* \* \* \*